(12) United States Patent
Jung et al.

(10) Patent No.: US 6,368,773 B1
(45) Date of Patent: Apr. 9, 2002

(54) PHOTORESIST CROSS-LINKER AND PHOTORESIST COMPOSITION COMPRISING THE SAME

(75) Inventors: Jae Chang Jung; Keun Kyu Kong; Myoung Soo Kim; Hyoung Gi Kim; Hyeong Soo Kim; Ki Ho Baik; Jin Soo Kim, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/448,916

(22) Filed: Nov. 24, 1999

(30) Foreign Application Priority Data

Nov. 27, 1998 (KR) .............................................. 98-51355
Feb. 22, 1999 (KR) .............................................. 99-5823

(51) Int. Cl.$^7$ .............................................. G03F 7/027
(52) U.S. Cl. .............................. 430/281.1; 430/270.1; 430/325
(58) Field of Search .......................... 430/270.1, 281.1, 430/325; 526/271, 317.1, 333; 568/594, 596

(56) References Cited

U.S. PATENT DOCUMENTS

| | | | |
|---|---|---|---|
| 2,866,813 A | * 12/1958 | McTeer | 260/488 |
| 3,468,857 A | 9/1969 | Graver | 260/80.3 |
| 4,562,009 A | * 12/1985 | Lysenko et al. | 260/465.6 |
| 4,579,979 A | * 4/1986 | Andrade et al. | 568/596 |
| 4,607,126 A | * 8/1986 | Sajtos | 568/385 |
| 5,200,051 A | * 4/1993 | Cozzette et al. | 204/403 |
| 5,290,894 A | * 3/1994 | Melrose et al. | 526/315 |
| 5,645,969 A | * 7/1997 | Matsuo et al. | 430/165 |
| 6,121,399 A | * 9/2000 | Webster et al. | 525/320 |
| 6,184,263 B1 | * 2/2001 | Narang et al. | 522/11 |

FOREIGN PATENT DOCUMENTS

| | | |
|---|---|---|
| DE | 3714276 A1 | 11/1988 |
| EP | 0 100 071 A2 | 2/1984 |
| GB | 695789 | 8/1953 |

OTHER PUBLICATIONS

Academic Press Dictionary of Science and Technology definitions of acetal, alkyl, carboxylic acid, ester and ketone.*

CA90:138248, Sastre et al, Angew. Makromol. Chem. 1978, 73, 25–33.*

U.S. application No. 09/448,964, Jung et al., filed Nov. 24, 1999.

Chemical Abstract No. 110:96578.

* cited by examiner

Primary Examiner—Rosemary Ashton
(74) Attorney, Agent, or Firm—Townsend and Townsend and Crew LLP

(57) ABSTRACT

The present invention relates to a cross-linker for photoresist compositions which is suitable for a photolithography process using KrF (248 mn), ArF (193 mn), E-beam, ion beam or EUV light sources. Preferred cross-linkers, according to the present invention, comprise a copolymer of (i) a compound represented by following Chemical Formula 1 and/or (ii) one or more compound(s) selected from the group consisting of acrylic acid, methacrylic acid and maleic anhydride.

<Chemical Formula 1>

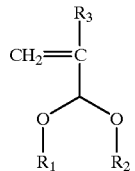

wherein, $R_1$ and $R_2$ individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; and $R_3$ represents hydrogen or methyl.

10 Claims, 12 Drawing Sheets

PHOTORESIST CROSS-LINKER AND PHOTORESIST COMPOSITION COMPRISING THE SAME

FIELD OF INVENTION

The present invention relates to cross-linking agents ("cross-linkers") usable for photoresist compositions, the polymers thereof, and photoresist compositions comprising the same. More specifically, it relates to cross-linking agents used in photoresists suitable for photolithography processes using a KrF (248 nm), ArF (193 nm), E-beam, ion beam or EUV light source when preparing a microcircuit of a highly integrated semiconductor element, and photoresist compositions employing the same.

BACKGROUND OF THE INVENTION

Recently, chemical amplification type DUV (deep ultra violet) photoresists have proven to be useful to achieve high sensitivity in processes for preparing micro-circuits in the manufacture of semiconductors. These photoresists are prepared by blending a photoacid generator with polymer matrix macromolecules having acid labile structures.

According to the reaction mechanism of such a photoresist, the photoacid generator generates acid when it is irradiated by the light source, and the main chain or branched chain of the polymer matrix macromolecule is cross-linked with the generated acid to form a cross-linked structure. Thus, the portion exposed to light cannot be dissolved by developing solution and remains unchanged, thereby producing a negative image of a mask on the substrate. In the lithography process, resolution depends upon the wavelength of the light source—the shorter the wavelength, the smaller the pattern that can be formed. However, when the wavelength of the light source is decreased in order to form a micro pattern [for example, in the case of using 193 nm wavelength or EUV (extremely ultraviolet) light], it is disadvantageous in that the lens of the exposing device is deformed by the light source, thereby shortening its life.

Melamine, a conventional cross-linker, has a limited number (three) of functional groups which can form a cross-linkage with acid. Further, a large amount of acid must be generated when melamine is used as a cross-linker, because acid is consumed by the cross-linking reaction. As a result, high energy light exposure is required for such cross-linking agents.

In order to overcome the disadvantages described above, chemical amplification type compounds that cross-link with a photoresist resin and use less amounts of energy are desirable. However, such chemical amplification type cross-linkers have not yet been developed.

Furthermore, in a pattern of high integrity, developing solution may be soaked into the cross-linked site, to swell up the cross-linked site. Thus, in order to form a pattern of higher integrity, the incorporation of a novel cross-linker, which performs cross-linking more elaborately, is required.

FIG. 1 shows a photoresist pattern that was formed by using a photoresist composition comprising a conventional cross-linker (J. Photopolymer Science and Technology, Vol.11, No.3, 1998, 507–512). The pattern is a 0.225 μm L/S pattern obtained by a photolithography process employing an ArF light source and a monomeric cross-linker.

As can be shown from FIG. 1, swelling occurs in a conventional photoresist pattern, so that a pattern of less than 0.225 μm L/S is difficult to obtain.

SUMMARY OF THE INVENTION

The object of the present invention is to provide a photoresist cross-linker, and a process for preparing the same.

Another object of the present invention is to provide a photoresist composition comprising a cross-linker, and a process for preparing the composition.

Still another object of the invention is to provide a semiconductor element manufactured by using the photoresist composition.

In order to achieve these objects, the present invention provides a cross-linker monomer that comprises a compound represented by following Chemical Formula 1:

<Chemical Formula 1>

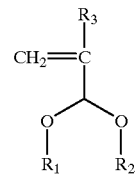

wherein, $R_1$ and $R_2$ individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; and $R_3$ represents hydrogen or methyl.

In order to achieve another object of the present invention, a photoresist composition is provided which comprises (i) a photoresist polymer, (ii) a photoresist cross-linker as described above, (iii) a photoacid generator and (iv) an organic solvent.

DETAILED DESCRIPTION OF THE INVENTION

Figure 1:
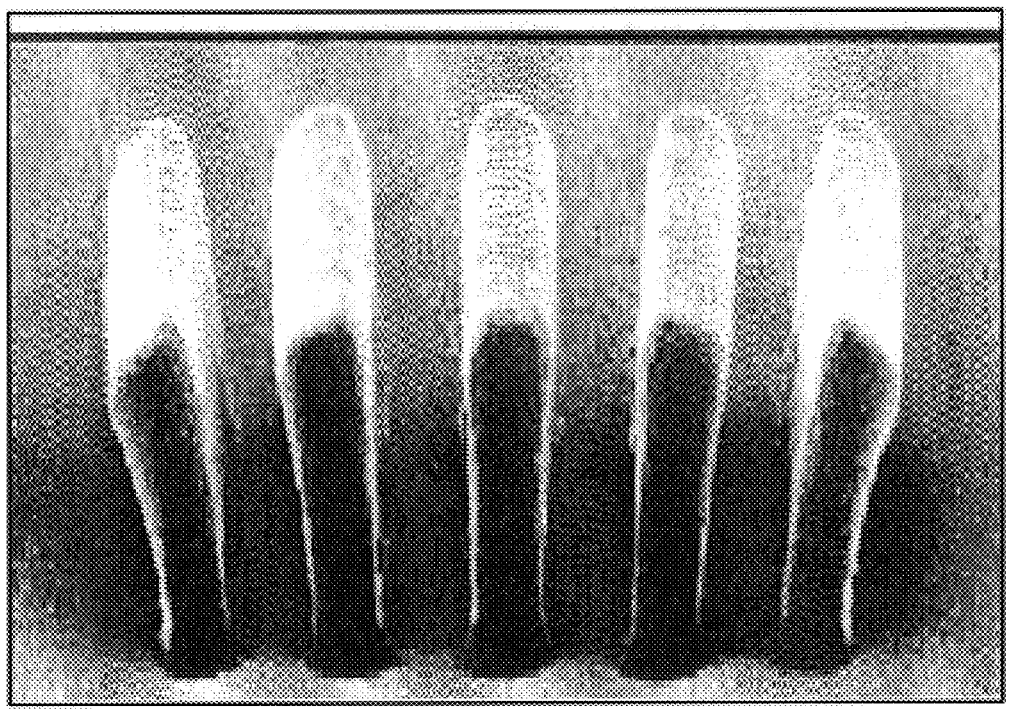
FIG. 1 shows a photoresist pattern prepared by using a conventional cross-linker.

The inventors have performed intensive studies to achieve the objects of the invention described above, and have found that compounds represented by the following Chemical Formula 1 have appropriate properties to serve as monomers in the formation of negative photoresist cross-linker polymers:

<Chemical Formula 1>

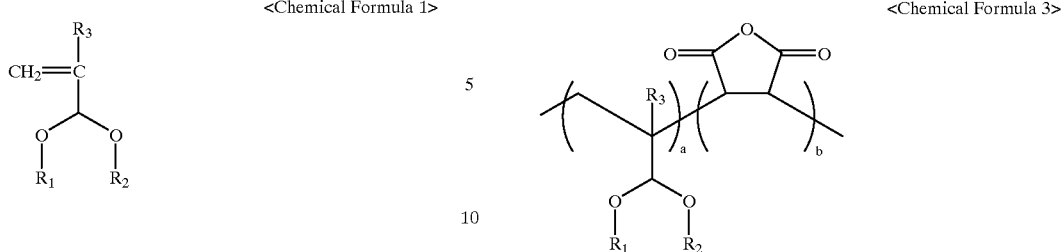

wherein, $R_1$ and $R_2$ individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; and $R_3$ represents hydrogen or methyl.

Cross-linker polymers having repeating units derived from compounds of Chemical Formula 1 react with photoresist resins having hydroxyl groups in the presence of acid, to induce a cross-linking reaction between the photoresist polymers. The compounds of the present invention are cross-linkers of the chemical amplification type, and therefore further combine with the photoresist resin to generate acid ($H^+$) to induce continuous chain cross-linking. Thus, the exposed portion of the photoresist resin can be cured to a high density in the course of the post-baking step of the semi-conductor manufacturing process, thereby obtaining an excellent pattern with low exposure energy.

The photoresist cross-linker according to the present invention may be a homopolymer of the compound represented by Chemical Formula 1; however, it is more preferable that the cross-linker is a copolymer of (i) the compound represented by Chemical Formula 1 and (ii) one or more compound(s) selected from the group consisting of acrylate, methacrylate and maleic anhydride, as the second comonomer. In this case, the cross-linker according to the present invention can be represented by following Chemical Formula 2 or Chemical Formula 3:

<Chemical Formula 2> wherein, $R_1$ and $R_2$ individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; $R_3$ and $R_4$ individually represent hydrogen or methyl; and a: b=10–100 mol %:0–90 mol %.

<Chemical Formula 3> wherein, $R_1$ and $R_2$ individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; $R_3$ represents hydrogen or methyl; and a: b=10–90 mol %:10–90 mol %.

The reaction mechanism of the cross-linkers according to the present invention is described with reference to Reaction Scheme 1 shown below.

First, a cross-linker polymer according to the present invention is mixed with a photoresist resin, and the mixture is coated on a conventional semiconductor substrate (stage 1). Then, when a predetermined region of the substrate is exposed to light, the exposed portion generates acid (stage 2). Due to the acid generated from the exposed portion, the cross-linker of the present invention and the photoresist combine together, and such cross-linking further generates acid, thereby carrying out continuous chain cross-linking (stage 3).

Reaction Scheme 1

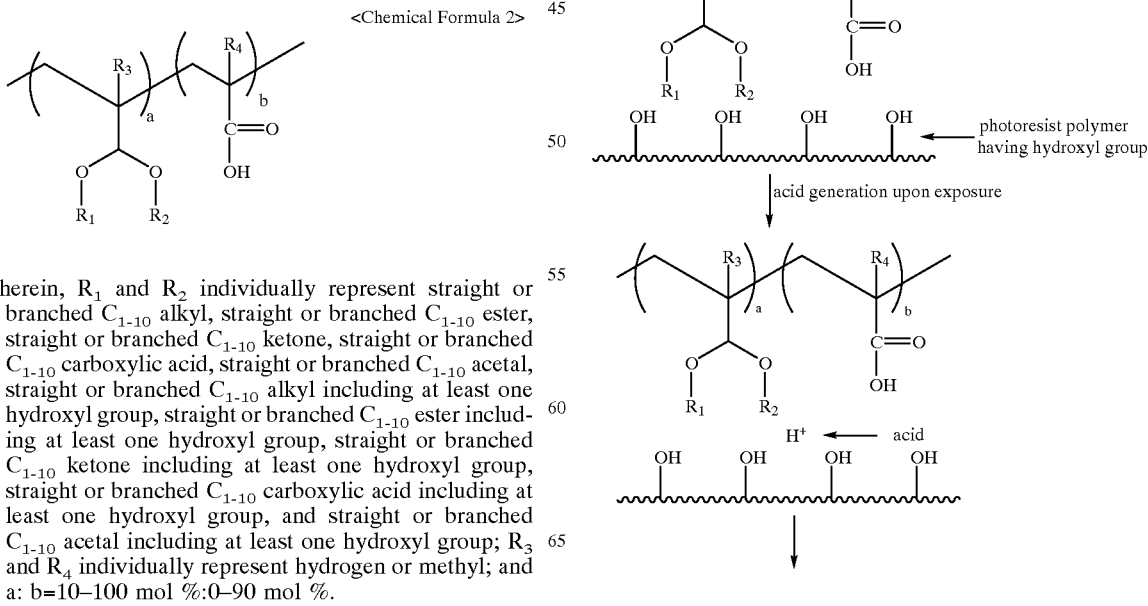

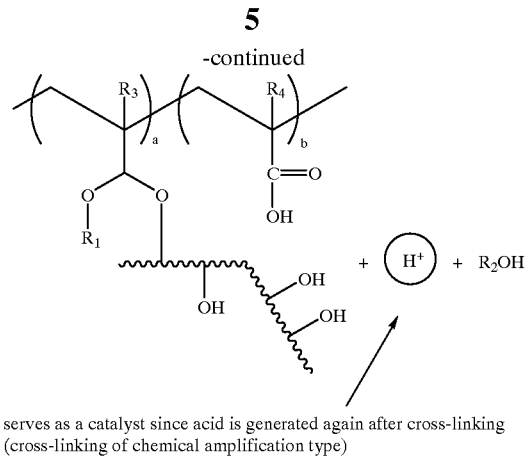

serves as a catalyst since acid is generated again after cross-linking (cross-linking of chemical amplification type)

Preparation of Cross-linkers

Preparation of cross-linking polymers according to the present invention is specifically described in Examples 1 to 8 below.

In Examples 1 to 8, AIBN was employed as a polymerization initiator, but other conventional radical polymerization initiators such as lauryl peroxide may be employed instead.

In the Examples, tetrahydrofuran was used as polymerization solvent, however, other solvents such as propylene glycol, toluene, methyl ether and acetate may be used instead.

Preparation of Photoresist Compositions

A process for preparing a negative photoresist composition using a cross-linker of the invention is described hereinbelow:

Since the cross-linkers of the present invention are chemical amplification type cross-linkers, photoresist compositions of the present invention comprise (i) a negative photoresist resin, (ii) a cross-linker according to the present invention, and (iii) a photoacid generator, together with (iv) an organic solvent in which these substances are mixed.

As the photoacid generator, sulfide or onium type compounds are preferably used. For example, the photoacid generator may be one or more compounds selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate and dibutylnaphthylsulfoniumn triflate.

As an organic solvent, cyclohexanone, methyl 3-methoxypriopionate, ethyl 3-ethoxypropionate, propylene glycol methyl ether acetate, or other conventional organic solvents may be used.

Formation of Photoresist Pattern

The photoresist composition prepared according to the present invention is spin-coated on a silicon wafer to form a thing, and the film is "soft-baked" in an oven or on a hot plate at 70 to 200° C., more preferably at 80 to 150° C. for 1 to 5 minutes. Then, the photoresist film is exposed to light by using a deep ultraviolet exposer or an excimer laser exposer, and then "post-baked" at 10 to 200° C., more preferably, at 100 to 200° C. As a light source, ArF light, KrF light, E-beam, X-ray, EUV (extremely ultraviolet), DTV (deep ultraviolet) or the like may be used. The exposure energy is preferably 0.1 to 100 mJ/cm².

Figure 2:
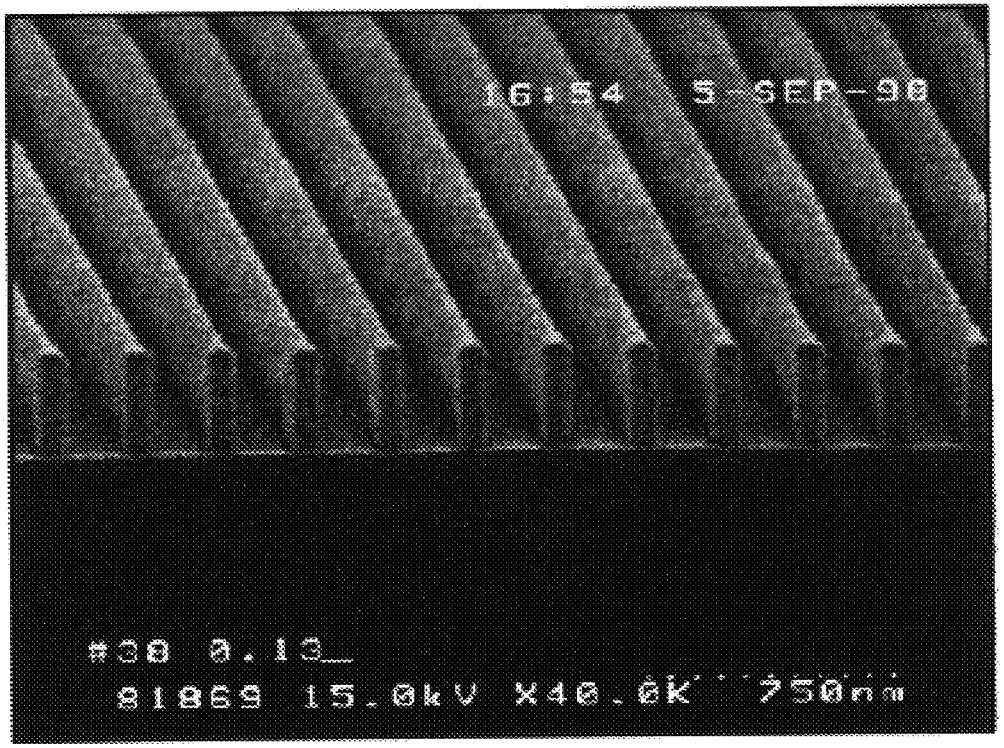
FIG. 2 to FIG. 12 show photoresist patterns prepared by using a cross-linker according to the present invention.

The exposed wafer is developed by impregnating the wafer in an alkaline developing solution such as 2.38 wt % or 2.5 wt % aqueous tetramethylammonium hydroxide (TMAH) solution for a predetermined time, preferably, for 1.5 minutes, to obtain an ultramicro pattern (FIG. 2).

When a photoresist composition is prepared by using the novel cross-linking agent according to the present invention, the difference in curability of the photoresist resin between the exposed portion and unexposed portion is pronounced, thereby obtaining a photoresist pattern having more excellent profile. Further, cross-linkers of the present invention can achieve sufficient results using only a small amount of photoacid generator, since the cross-linker is a chemical amplification type. Thus, the problems caused by using a large amount of photoacid generator can be overcome. The photoresist composition shows excellent light sensitivity, therefore sufficient exposure can be achieved by using low irradiating energy for exposure. Accordingly, it is suitable for photolithography employing a light source of extremely short wavelength, such as ArF (193 mn).

DESCRIPTION OF THE SPECIFIC EMBODIMENTS

The invention is described in more detail by referring to the examples below, but it should be noted that the present invention is not restricted to these examples.

EXAMPLE 1

Synthesis of Poly(3,3-dimethoxypropene)

Acrolein (30 g) represented by Chemical Formula 4 below, AIBN (0.6 g) and tetrahydrofuran (75 g) were placed in a 200 ml flask, and reacted at 65° C. under nitrogen or argon atmosphere for 8 hours. After the polymerization was completed, polyacrolein was precipitated from ethyl ether (yield: 60%).

Polyacrolein thus obtained (20 g) and methanol (200 g) were placed in a 500-ml round-bottomed flask, and closely mixed. Trifluoromethanesulfonic acid (0.5 g) was added thereto, and the resultant mixture was heated under reflux at 80° C. for 24 hours, then neutralized to pH 7–8 using TMAH solution. Then, the reaction mixture was concentrated by using a rotary evaporator, and the residue was precipitated from distilled water. The precipitate was dried in vacuo to obtain poly(3,3-dimethoxypropene) resin of Chemical Formula 5 (yield: 60%). The compound of Chemical Formula 5 was confirmed on an NMR spectrum thereof by the disappearance of an aldehyde peak at 8 to 9 ppm. The molecular weight of the compound of Chemical Formula 5 is preferably within the range of 4,000 to 6,000.

<Chemical Formula 4>

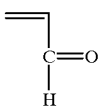

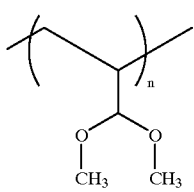

<Chemical Formula 5>

In the formula, n represents the number of monomers participating in the homopolymerization.

EXAMPLE 2

Synthesis of Poly(3,3-dimethoxypropene/acrylic acid)

Acrolein of Chemical Formula 4 (30 g), acrylic acid (3 g), AIBN (0.66 g) and tetrahydrofuran (80 g) were placed in a 200 ml flask, and the mixture was reacted at 60° C. under nitrogen or argon atmosphere for 8 hours. After the polymerization was completed, polymers were obtained by precipitating from water (16 g, yield: 50%) The polymers thus obtained (16 g) and methanol (300 g) were placed in a round-bottomed flask, and closely mixed. Trifluoromethane-sulfonic acid (0.8 ml) was added thereto, and the resultant mixture was heated under reflux at 80° C. for 8 hours, then neutralized to pH 7–8 using TMAH solution. Then, the reaction mixture was concentrated by using a rotary evaporator, and the resultant solution was dissolved in chloroform (300 g). The solution was placed in a separating funnel, and distilled water (300 g) was added thereto. Then the distilled water layer was separated and concentrated by evaporation under reduced pressure to obtain poly(3,3-dimethoxypropene/acrylic acid) resin of Chemical Formula 6 (yield: 70%, molecular weight: 4000 to 7000).

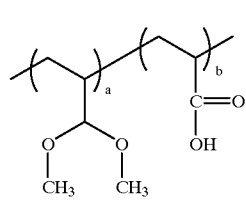

<Chemical Formula 6>

In the formula, a and b individually represent the polymerization ratio of each comonomer.

EXAMPLE 3

Synthesis of Poly(3,3-diethoxypropene)

The procedure according to Example 1 was repeated but using ethanol instead of methanol, to obtain the compound represented by Chemical Formula 7, poly(3,3-diethoxypropene) (yield: 67%).

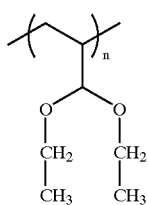

<Chemical Formula 7>

In the formula, n represents the number of monomers participating in the homopolymerization.

EXAMPLE 4

Synthesis of Poly(3,3-diethoxypropene/acrylic acid)

The procedure according to Example 2 was repeated but using ethanol instead of methanol, to obtain the compound represented by Chemical Formula 8, poly(3,3-diethoxypropene/acrylic acid) (yield: 67%).

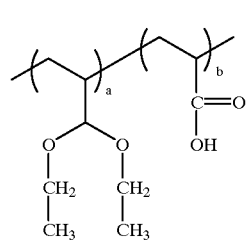

<Chemical Formula 8>

In the formula, a and b individually represent the polymerization ratio of each comonomer.

EXAMPLE 5

Synthesis of Poly(3,3-dimethoxypropene/maleic anhydride)

3,3-dimethoxypropene of Chemical Formula 9 (0.3 mole), maleic anhydride (0.1 mole), AIBN (0.8 g) and tetrahydrofuran (42 g) were placed in a 100 ml flask and the mixture was reacted at 65° C. under nitrogen or argon atmosphere for 8 hours. After the polymerization was completed, the polymers were precipitated from ethyl ether. The polymer precipitate was dried in vacuo to obtain pure resin represented by following Chemical Formula 10:

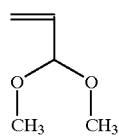

<Chemical Formula 9>

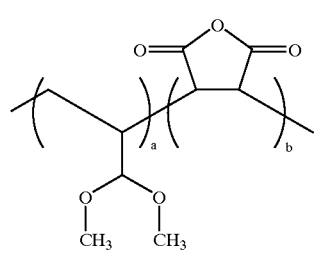

<Chemical Formula 10> wherein, a and b individually represent the polymerization ratio of each comonomer.

EXAMPLE 6

Synthesis of Poly(3,3-diethoxypropene/maleic anhydride)

The procedure according to Example 5 was repeated but using 3, 3-diethoxypropene (0.3 mole) of Chemical Formula 11 instead of 3, 3-dimethoxypropene (0.3 mole) of Chemical Formula 9, to obtain the compound represented by Chemical Formula 12 (yield: 51%).

<Chemical Formula 11>

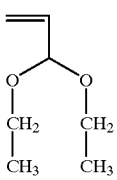

<Chemical Formula 12>

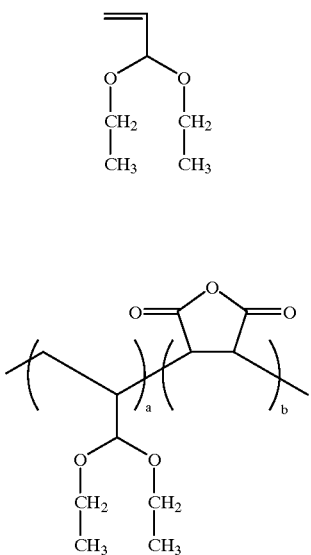

In the formula, a and b individually represent the polymerization ratio of each comonomer.

EXAMPLE 7

Synthesis of Poly(3,3-dimethoxy-2-methylpropene)

The procedure according to Example 1 was repeated but using methacrolein instead of acrolein to obtain the compound represented by Chemical Formula 13, poly(3,3-dimethoxy-2-methylpropene).

<Chemical Formula 13>

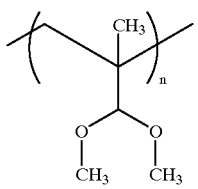

In the formula, n represents the number of monomers participating the homopolymerization.

EXAMPLE 8

Synthesis of poly(3,3-diethoxy-2-methylpropene)

The procedure according to Example 3 was repeated but using methacrolein instead of acrolein to obtain the compound represented by Chemical Formula 14, poly(3,3-diethoxy-2-methylpropene).

<Chemical Formula 14>

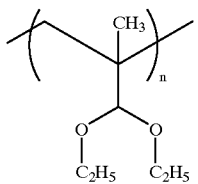

In the formula, n represents the number of monomers participating the homopolymerization.

EXAMPLE 9

(i) The photoresist resin represented by following Chemical Formula 15, that is, poly(bicyclo[2.2.1]hept-5-ene/2-hydroxyethylbicyclo[2.2.1]hept-5-ene 2-carboxylate/maleic anhydride) (20 g), (ii) poly(3,3,-dimethoxypropene) cross-linker obtained from Example 1 of the present invention (5 g), and (iii) triphenylsulfonium triflate as a photoacid generator (0.6 g) were dissolved in propylene glycol methyl ether acetate (200 g) as an organic solvent, to prepare a photoresist composition.

<Chemical Formula 15>

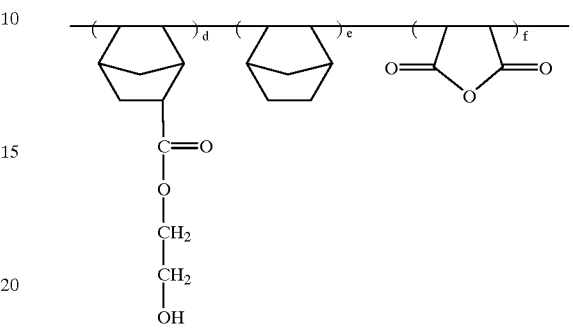

Figure 3:
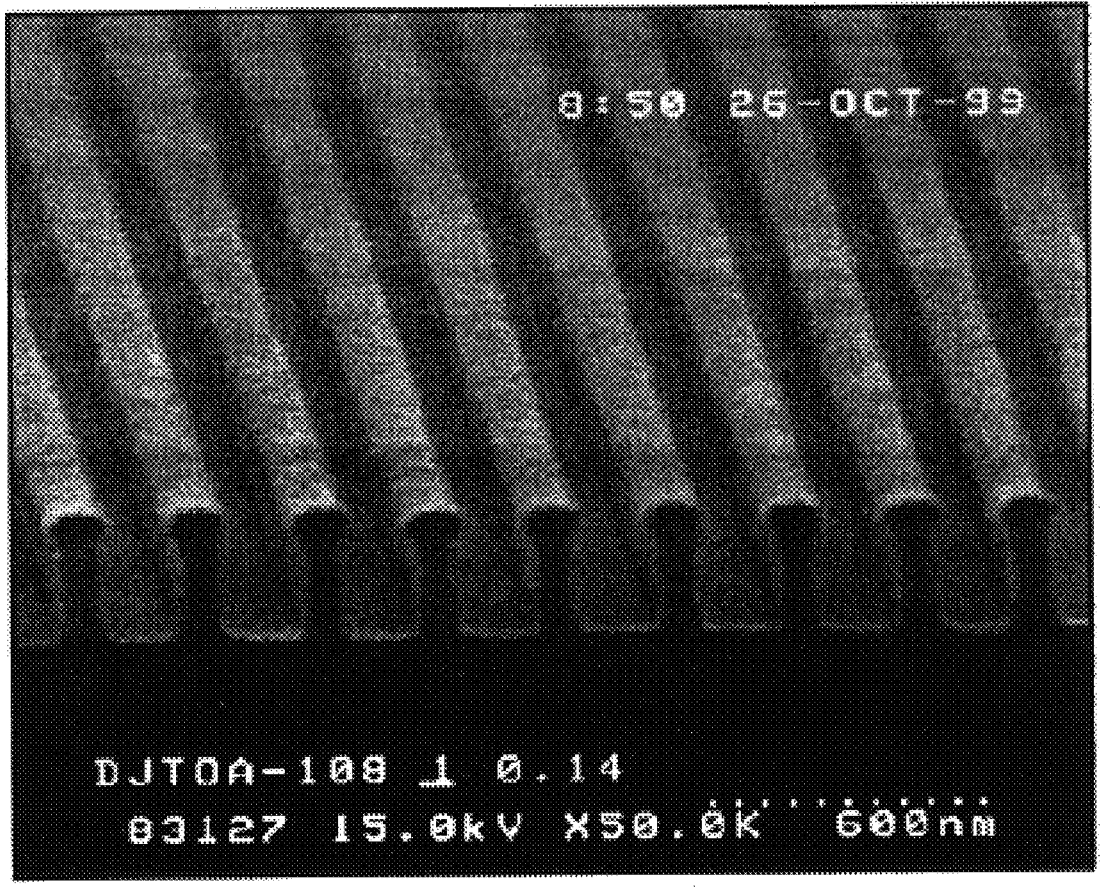

The photoresist composition thus prepared was coated on a silicon wafer, and soft-baked at 110° C. for 90 seconds, exposed to light by using ArF exposer, post-baked at 110° C. for 90 seconds, and then developed with 2.38 wt % TMAH developing solution. As a result, a 0.13 μm L/S ultramicro negative pattern was obtained, as illustrated in FIG. 3.

The exposure energy for this example was 18 mJ/cm$^2$. The curing sensitivity of the photoresist composition was excellent even with the exposure energy of such minute intensity. As can be shown in FIG. 1, no swelling was observed. The results are due to the excellent curability of poly(3,3 -dimethoxypropene) resin, a cross-linker according to the present invention, and the intimate cross-linking resulting therefrom. Thus, the ultramicro pattern shows excellent pattern profile.

EXAMPLE 10

(i) The photoresist resin represented by Chemical Formula 15, that is, poly(bicyclo[2.2.1]hept-5-ene/2-hydroxyethylbicyclo[2.2.1]hept-5-ene 2-carboxylate/maleic anhydride) (20 g), (ii) poly(3,3,-dimethoxypropene/acrylic acid) cross-linker obtained from Example 2 of the present invention (20 g), and (iii) triphenylsulfonium triflate as a photoacid generator (0.7 g) were dissolved in propylene glycol methyl ether acetate (200 g) as an organic solvent, to prepare a photoresist composition.

Figure 4:
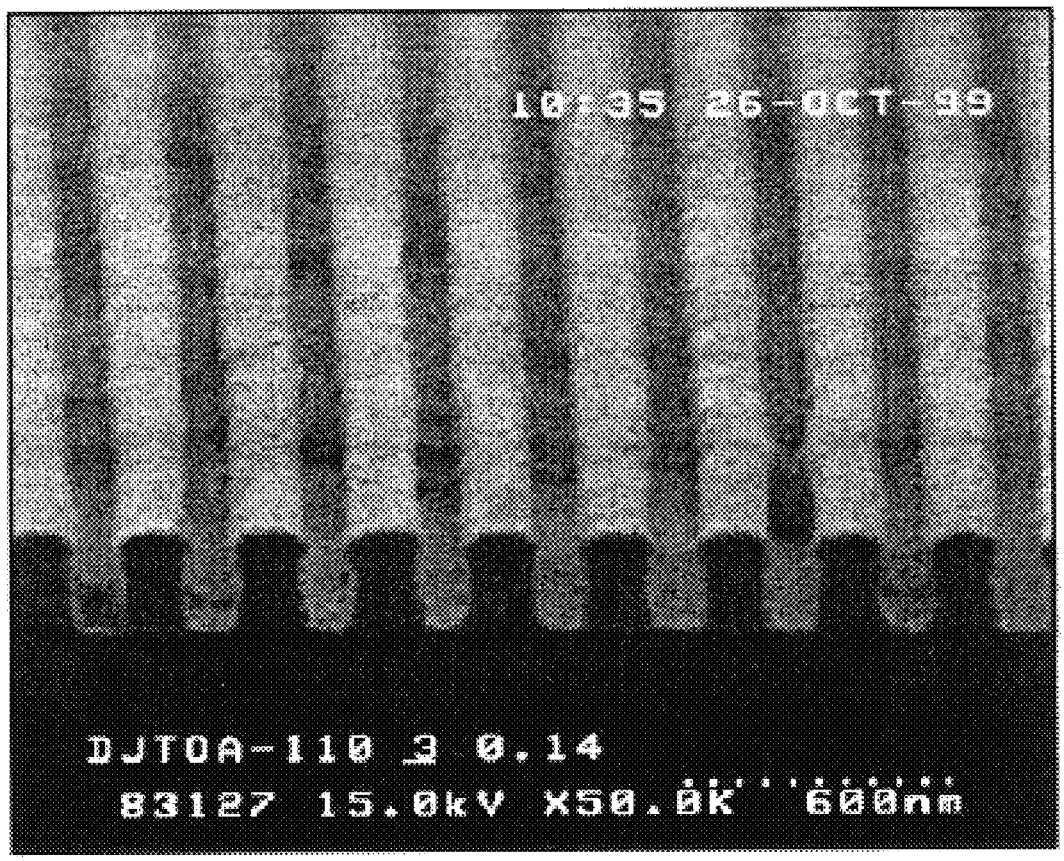
Figure 5:
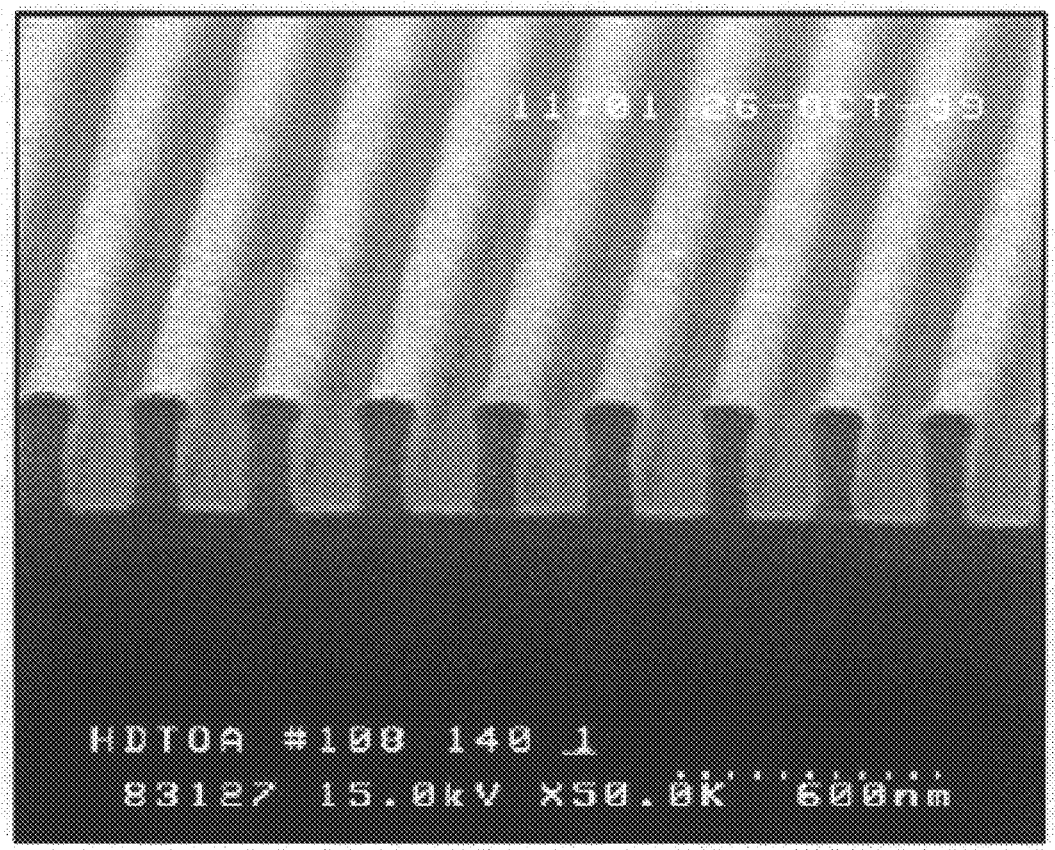
Figure 6:
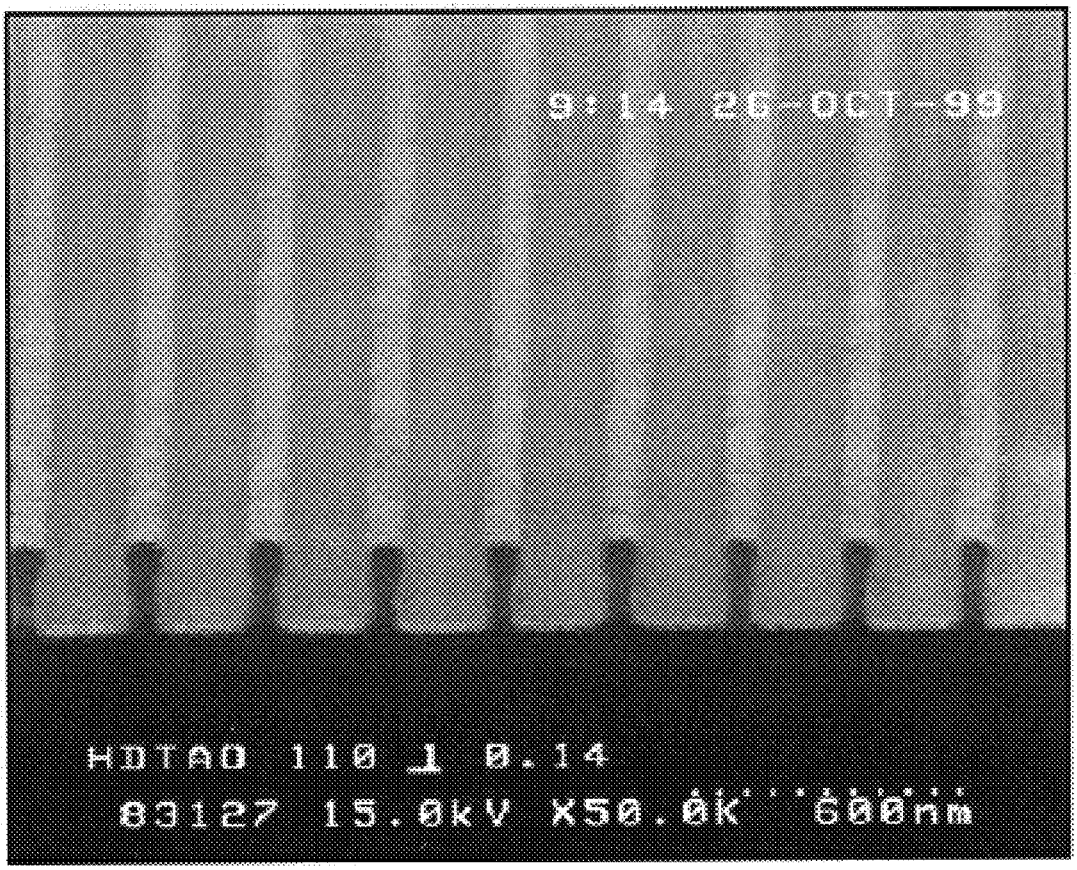
Figure 7:
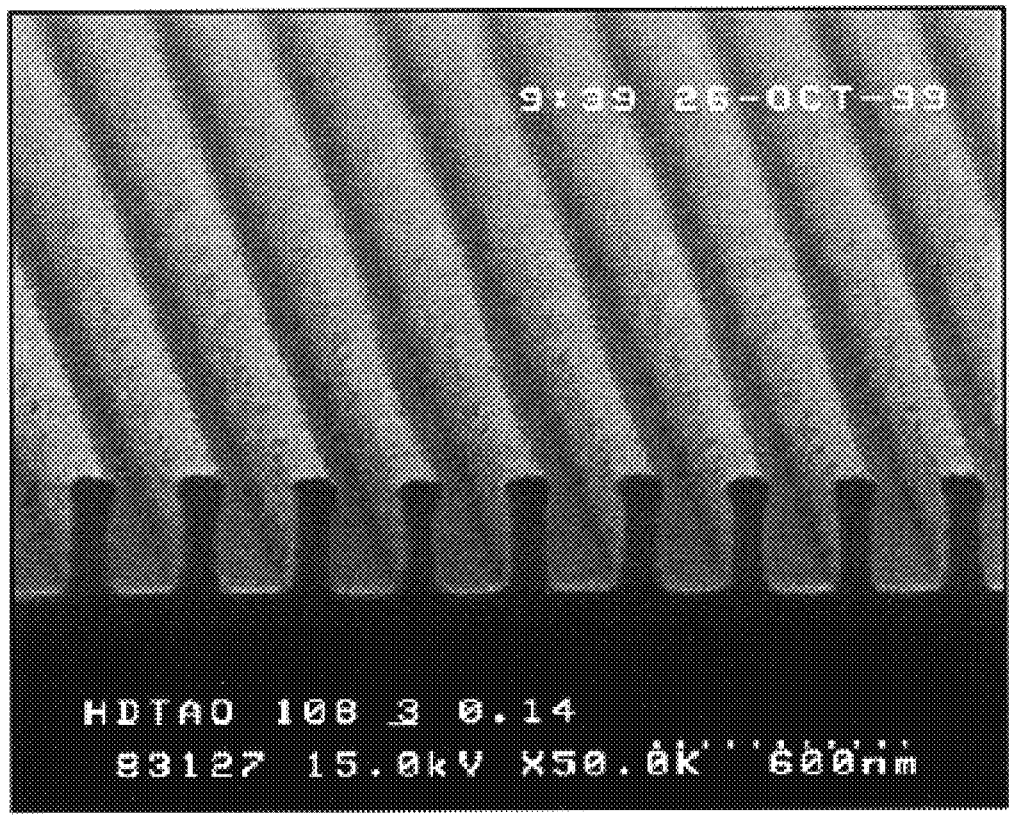
Figure 8:
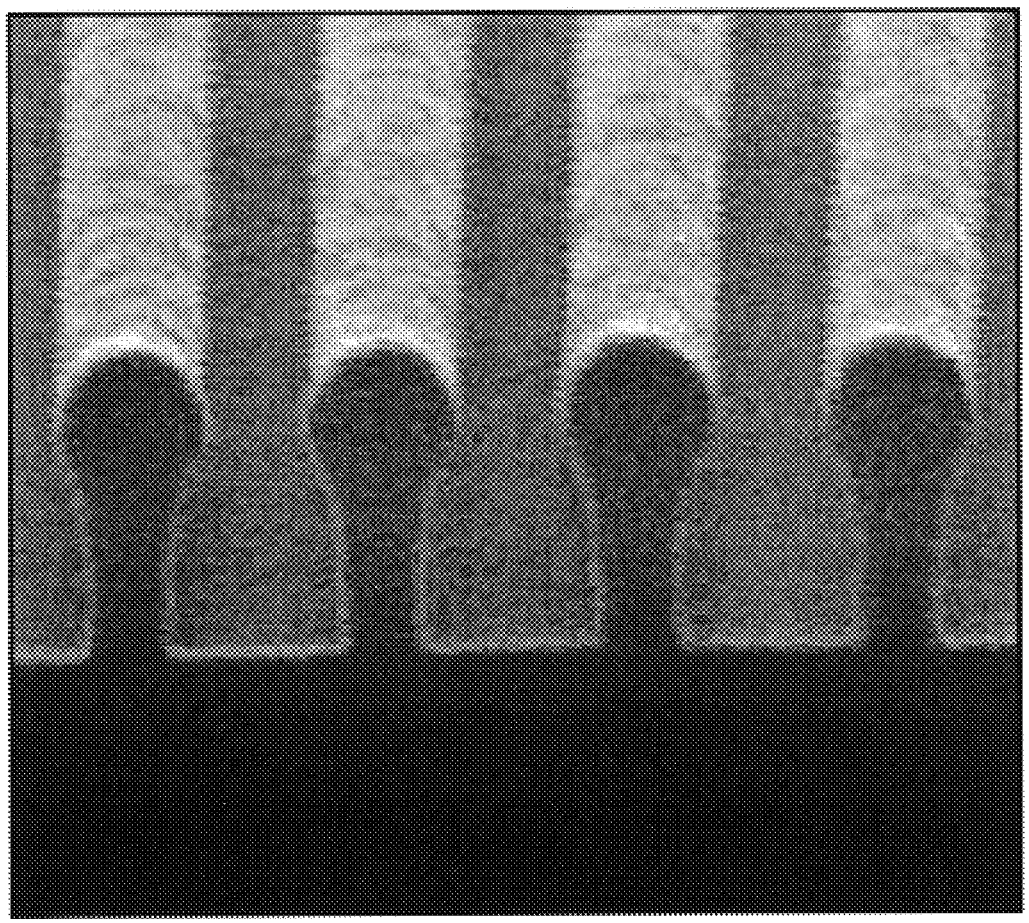
Figure 9:
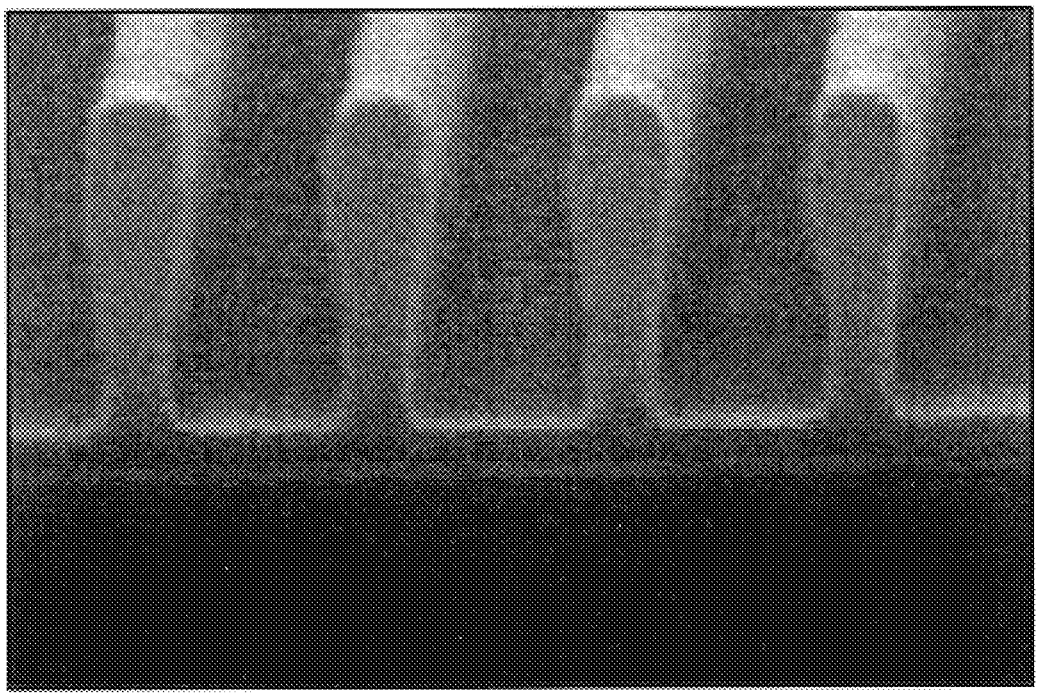
Figure 10:
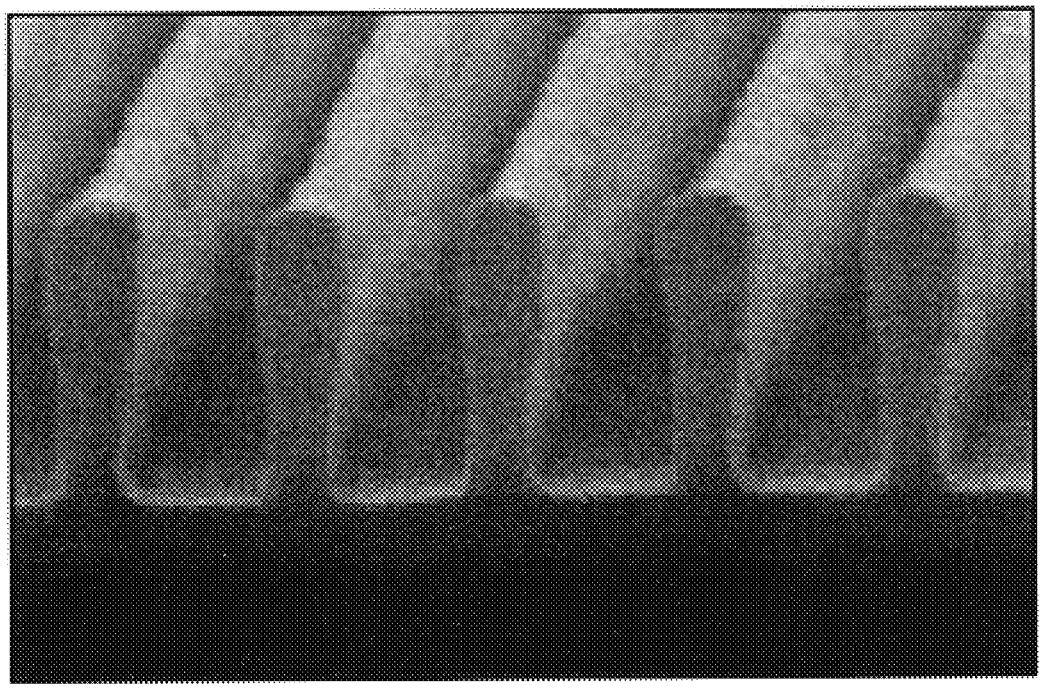

The photoresist composition thus prepared was coated on a silicon wafer, and soft-baked at 110° C. for 90 seconds, exposed to light by using ArF exposer, post-baked at 110° C. for 90 seconds, and then developed with 2.38 wt % TMAH developing solution, to obtain a 0.13 μm L/S ultramicro negative pattern. In this example also, even though the exposure energy was very weak (18 mJ/cm$^2$), as in Example 1, an ultramicro pattern having an excellent pattern profile was obtained (FIG. 4).

EXAMPLE 11–16

The same procedures were repeated for the cross-linkers obtained from Example 3 to Example 8, and as a result, excellent micro patterns were obtained as in Example 9 and 10 (FIG. 5 to FIG. 10).

EXAMPLE 17

(i) The photoresist resin represented by Chemical Formula 16 (20 g), (ii) poly(3,3,-dimethoxypropene/acrylic acid) cross-linker obtained from Example 2 of the present invention (10 g), and (iii) triphenylsulfonium triflate as a photoacid generator (0.6 g) were dissolved in propylene glycol methyl ether acetate (200 g) as an organic solvent, to prepare a photoresist composition.

Figure 11:
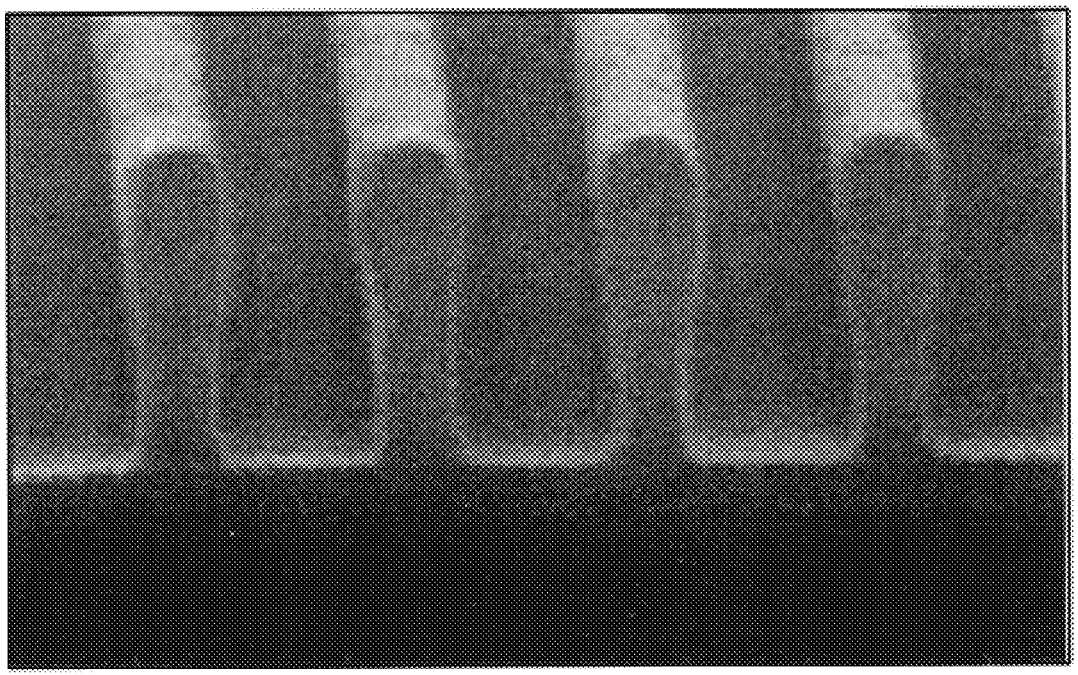

The photoresist composition thus prepared was coated on a silicon wafer, and soft-baked at 110° C. for 90 seconds, exposed to light by using ArF exposer, post-baked at 110° C. for 90 seconds, and then developed with 2.38 wt % TMAH developing solution, to obtain a 0.13 μm L/S ultramicro negative pattern. In this example also, even though the exposure energy was very weak (15 mJ/cm$^2$) as in Example 1, an ultramicro pattern having excellent pattern profile was obtained (FIG. 11).

<Chemical Formula 16>

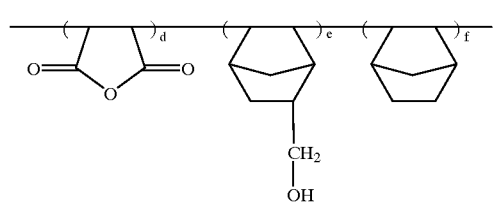

EXAMPLE 18

Figure 12:
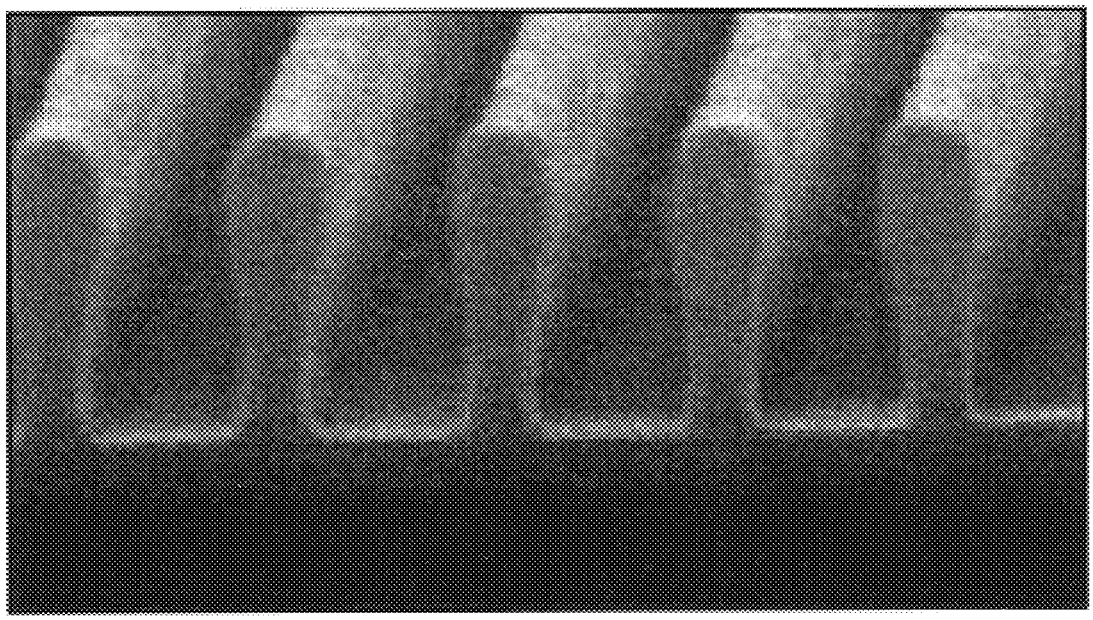

The procedure according to Example 17 was repeated but using the photoresist resin of Chemical Formula 17 instead of the resin of Chemical Formula 16 to obtain a 0.18 μm L/S ultramicro negative pattern (FIG. 12).

<Chemical Formula 17>

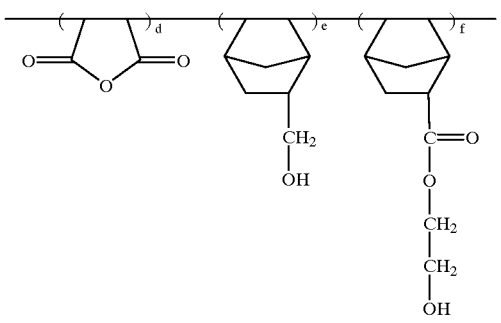

EXAMPLE 19

The procedure according to Example 17 was repeated but using the photoresist resin of Chemical Formula 18 instead of the resin of Chemical Formula 16 to obtain a 0.20 μm L/S ultramicro negative pattern.

<Chemical Formula 18>

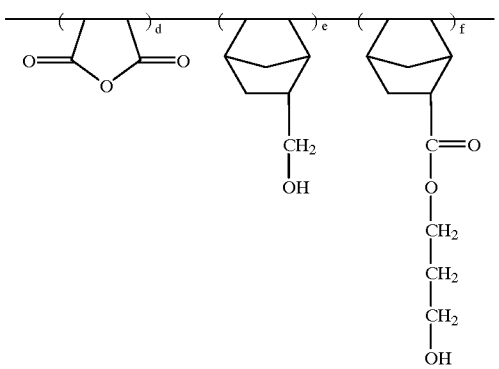

EXAMPLE 20

The procedure according to Example 17 was repeated but using the photoresist resin of Chemical Formula 19 instead of the resin of Chemical Formula 16 to obtain a 0.20 μm L/S ultramicro negative pattern.

<Chemical Formula 19>

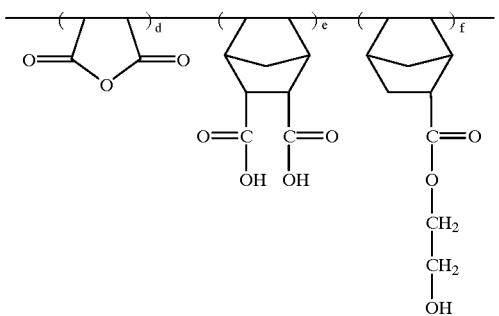

EXAMPLE 21

The procedure according to Example 17 was repeated but using the photoresist resin of Chemical Formula 20 instead of the resin of Chemical Formula 16 to obtain a 0.20 μm L/S ultramicro negative pattern.

<Chemical Formula 20>

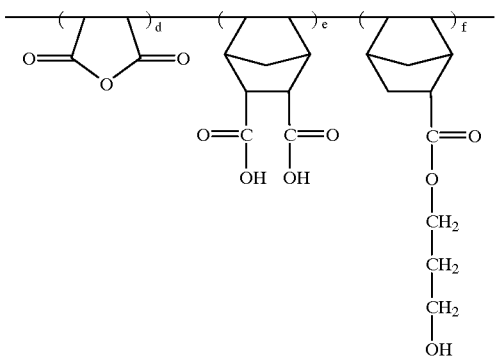

What is claimed is:

1. A photoresist composition which comprises (i) a photoresist polymer, (ii) at least one cross-linking substance selected from the group consisting of a monomer represented by the following Chemical Formula 1, its homopolymer, its copolymers, and mixtures thereof:

<Chemical Formula 1>

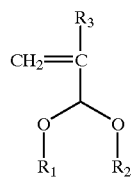

wherein, $R_1$ and $R_2$ individually represent unsubstituted straight or branched $C_{1-10}$ alkyl, straight or branched $C_{1-10}$ alkyl substituted with at least one ester group, straight or branched $C_{1-10}$ alkyl substituted with at least one ketone group, straight or branched $C_{1-10}$ alkyl substituted with at least one carboxylic acid group, straight or branched $C_{1-10}$ alkyl substituted with at least one acetal group, straight or branched $C_{1-10}$ alkyl substituted with at least one hydroxyl group, straight or branched $C_{1-10}$ alkyl substituted with at least one hydroxyl group and one ester group, straight or branched $C_{1-10}$ alkyl substituted with at least one hydroxyl group and one ketone group, straight or branched $C_{1-10}$ alkyl substituted with at least one hydroxyl group and one carboxylic acid group, and straight or branched $C_{1-10}$ alkyl substituted with at least one hydroxyl group and one acetal group; and $R_3$ represents hydrogen or methyl; (iii) a photoacid generator; and (iv) an organic solvent.

2. A photoresist composition according to claim 1, wherein the photoresist polymer comprises hydroxyl groups.

3. A photoresist composition according to claim 2, wherein the photoresist polymer is selected from the group consisting of the compounds represented by following Chemical Formula 15 to 20:

<Chemical Formula 15>

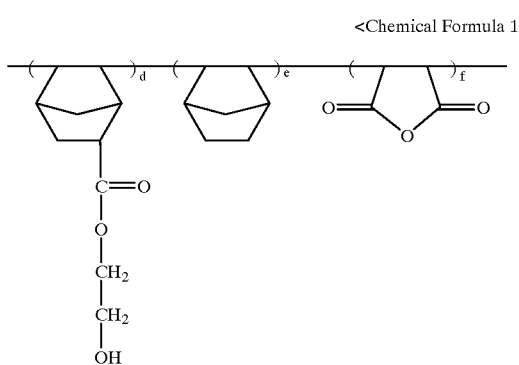

<Chemical Formula 16>

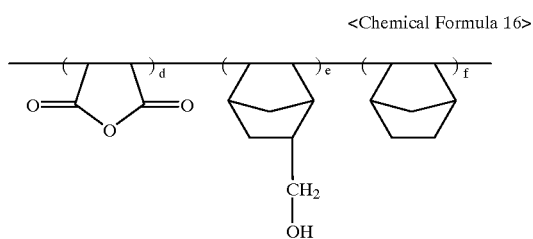

<Chemical Formula 17>

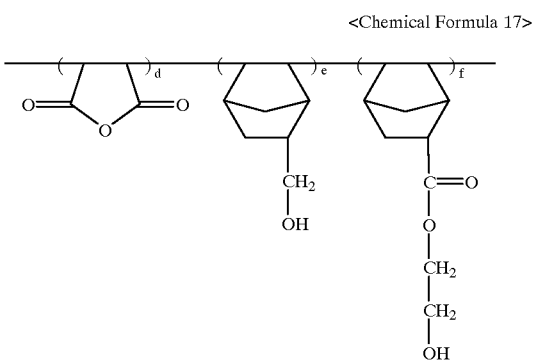

<Chemical Formula 18>

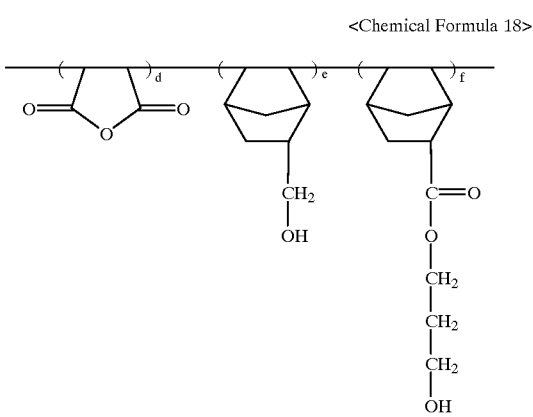

<Chemical Formula 19>

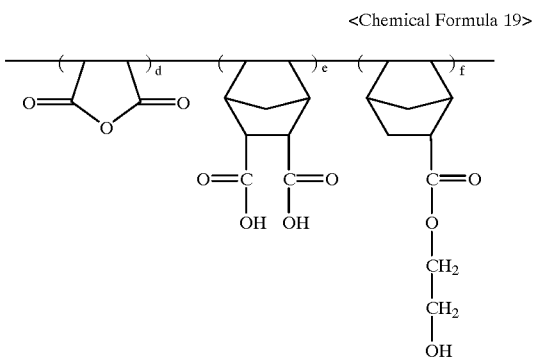

<Chemical Formula 20>

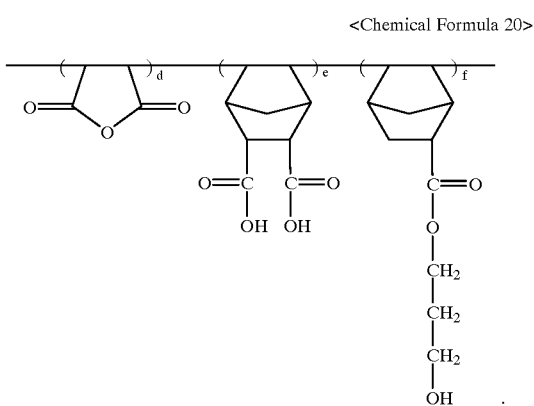

4. A photoresist composition according to claim 1, wherein the photoacid generator is one or more compound(s) selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate and dibutylnaphthylsulfonium triflate.

5. A photoresist composition according to claim 1, wherein the organic solvent is selected from the group consisting of cyclohexanone, methyl 3-methoxypropionate, ethyl 3-ethoxypropionate and propylene glycol methyl ether acetate.

6. A process for forming a photoresist pattern, which comprises the steps of (a) coating the composition of claim 1 on a wafer, (b) exposing the wafer to light by employing an exposer, and (c) developing the exposed wafer.

7. A process according to claim 6, wherein the light source is selected from the group consisting of ArF (193 nm), KrF (248 nm), E-beam, X-ray, EUV and DUV (deep ultraviolet).

8. A process according to claim 6, wherein the developing step is carried out by using an alkaline developing solution.

9. A process according to claim 8, wherein the alkaline developing solution is 2.38 wt % or 2.5 wt % aqueous TMAH solution.

10. A semiconductor element manufactured by the process according to claim 6.

* * * * *

UNITED STATES PATENT AND TRADEMARK OFFICE
CERTIFICATE OF CORRECTION

PATENT NO.    : 6,368,773 B1
DATED         : April 9, 2002
INVENTOR(S)   : Jae Chang Jung et al.

It is certified that error appears in the above-identified patent and that said Letters Patent is hereby corrected as shown below:

Column 5,
Lines 52-53, the phrase "triphenylsulfonium triflate and dibutylnaphthylsulfoniumn triflate" should read -- triphenylsulfonium triflate and dibutylnaphthylsulfonium triflate --.
Lines 60-64, the sentence "The photoresist composition prepared according to the present invention is spin-coated on a silicon wafer to form a thing, and the film is "soft-baked" in an oven or on a hot plate at 70 to 200º C., more preferably at 80 to 150º C. for 1 to 5 minutes." should read -- The photoresist composition prepared according to the present invention is spin-coated on a silicon wafer to form a thin film, and the film is "soft-baked" in an oven or on a hot plate at 70 to 200º C., more preferably at 80 to 150º C. for 1 to 5 minutes. --.

Signed and Sealed this

Thirtieth Day of March, 2004

JON W. DUDAS
*Acting Director of the United States Patent and Trademark Office*